(12) United States Patent
Summerer

(10) Patent No.: US 7,976,563 B2
(45) Date of Patent: Jul. 12, 2011

(54) MEDICAL INSTRUMENT

(75) Inventor: Sabine Summerer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 340 days.

(21) Appl. No.: 11/776,282

(22) Filed: Jul. 11, 2007

(65) Prior Publication Data
US 2008/0015634 A1    Jan. 17, 2008

(30) Foreign Application Priority Data
Jul. 11, 2006    (DE) .......................... 10 2006 031 971

(51) Int. Cl.
*A61B 17/00*    (2006.01)
(52) U.S. Cl. ........................................ 606/208; 606/205
(58) Field of Classification Search .................... 81/345, 81/348, 361–363; 606/90, 174, 220, 205–208, 606/218–219; 600/218, 220
See application file for complete search history.

(56) References Cited

U.S. PATENT DOCUMENTS

| | | | | |
|---|---|---|---|---|
| 5,496,347 | A * | 3/1996 | Hashiguchi et al. | 606/205 |
| 5,722,988 | A * | 3/1998 | Weisshaupt | 606/205 |
| 5,906,630 | A | 5/1999 | Anderhub et al. | |
| 5,919,206 | A | 7/1999 | Gengler et al. | |
| 5,968,074 | A * | 10/1999 | Prestel | 606/205 |
| 6,063,103 | A * | 5/2000 | Hashiguchi | 606/205 |
| 6,146,394 | A * | 11/2000 | Morejohn et al. | 606/158 |
| 6,238,414 | B1 * | 5/2001 | Griffiths | 606/205 |
| 6,685,715 | B2 * | 2/2004 | Danitz et al. | 606/157 |
| 6,716,232 | B1 * | 4/2004 | Vidal et al. | 606/205 |
| 6,887,240 | B1 * | 5/2005 | Lands et al. | 606/51 |
| 7,494,501 | B2 * | 2/2009 | Ahlberg et al. | 606/207 |
| 7,566,334 | B2 * | 7/2009 | Christian et al. | 606/51 |
| 2001/0041912 | A1 * | 11/2001 | Ouchi | 606/205 |
| 2002/0183784 | A1 * | 12/2002 | Lutze et al. | 606/206 |
| 2005/0101991 | A1 * | 5/2005 | Ahlberg et al. | 606/205 |

FOREIGN PATENT DOCUMENTS

| | | |
|---|---|---|
| DE | 297 13 150 | 9/1997 |
| DE | 299 11 011 | 9/1999 |
| DE | 198 13 781 | 10/1999 |
| DE | 101 11 766 | 10/2002 |
| WO | 02071956 A1 | 9/2002 |

OTHER PUBLICATIONS

German Search Report, Jan. 9, 2007, 4 pages.
European Search Report, EP07013544, Oct. 31, 2007, 9 pages.

* cited by examiner

*Primary Examiner* — Gary Jackson
*Assistant Examiner* — Erin Colello
(74) *Attorney, Agent, or Firm* — St. Onge Steward Johnston & Reens LLC

(57) ABSTRACT

The invention relates to a medical instrument having on its proximal end a shaft with a handle consisting of two gripping members and on its distal end a tool consisting of two jaw members and in which, to open and close the tool, at least one jaw member can rotate with respect to the other jaw member around a point of rotation by means of a push-pull rod and in which the push-pull rod is connected on the proximal side with a rotatable gripping member of the handle. To produce a medical instrument that can be used even in closely confined spaces and with sufficient transmission of force, it is proposed with the invention that the point of rotation should be configured as a variable, virtual point of rotation that is dependent on the position of the jaw members to one another.

8 Claims, 6 Drawing Sheets

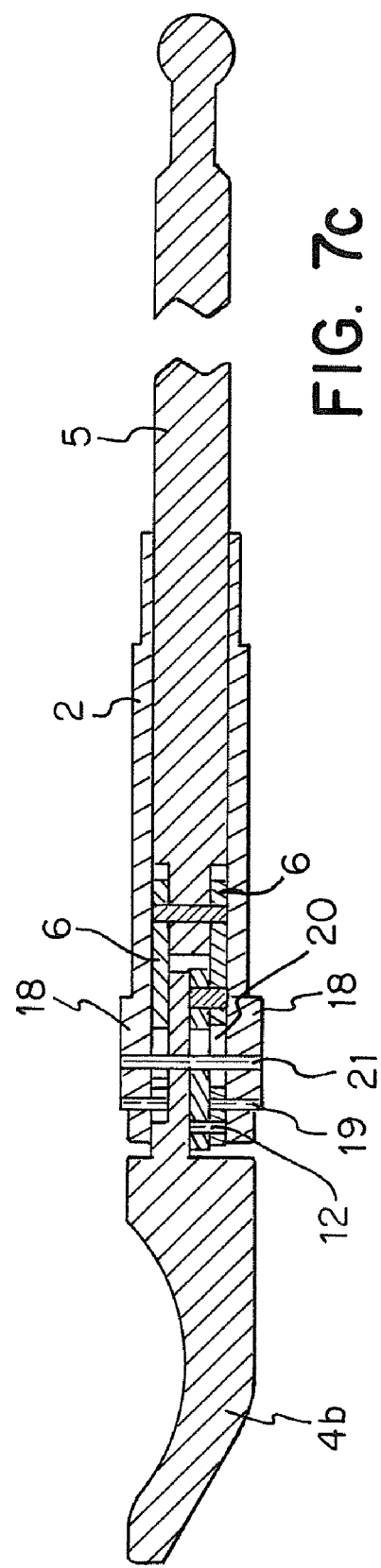

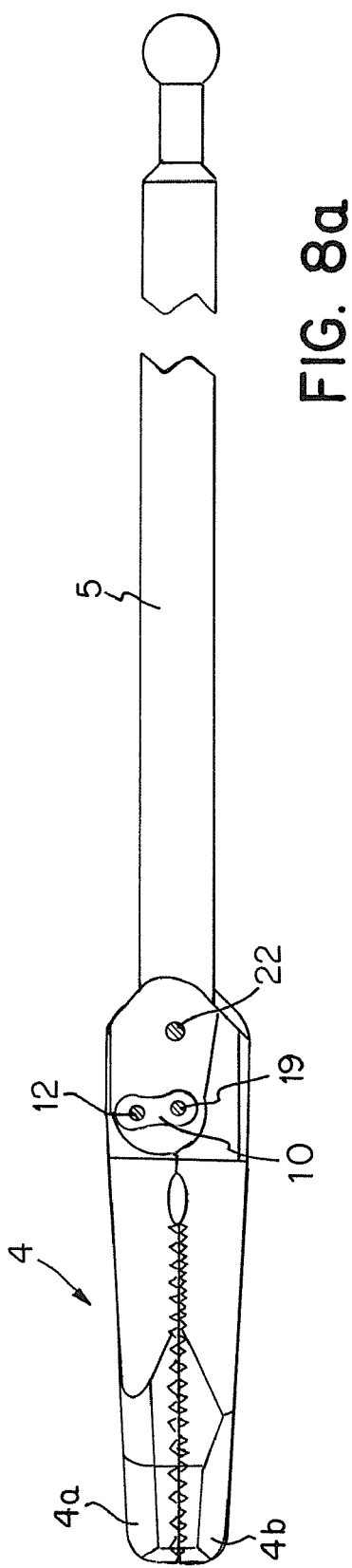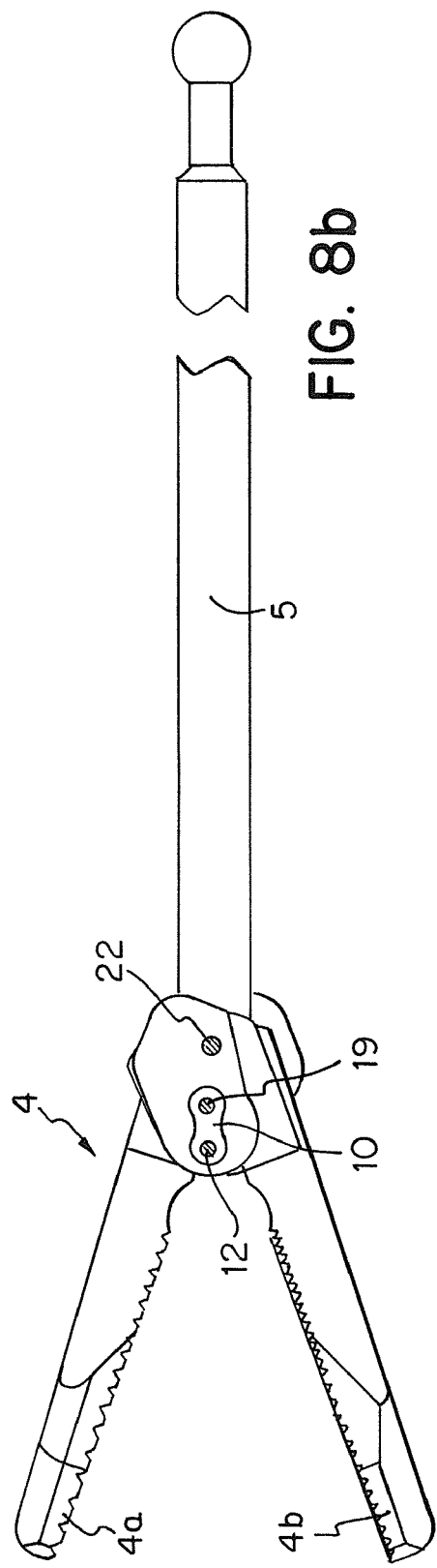

MEDICAL INSTRUMENT

FIELD OF THE INVENTION

The invention relates to a medical instrument having on its proximal end a shaft with a handle consisting of two gripping members and on its distal end a tool consisting of two jaw members and in which at least one jaw member can rotate with respect to the other jaw member around a point of rotation by means of a push-pull rod to open and close the tool and in which the push-pull rod is connected on the proximal side with a rotatable gripping member of the handle.

BACKGROUND OF THE INVENTION

Generic medical instruments are often used in the art as gripping, holding, and/or cutting tools. Thus the jaw members can comprise blades for severing tissue or blunt surfaces for holding severed tissue, for instance, or to clamp off blood vessels.

A common element among these medical instruments is that both jaw members of the tool mounted on the distal end of the shaft can rotate around a common point of rotation. For opening and closing the jaw members, a push-pull rod is provided which is coupled with a movable gripping member of the handle.

Such a generic medical instrument is described for instance, in DE 299 11 011 U. In this known medical instrument the coupling points of the jointed gear are contiguous with the respective jaw members at a distance from the common point of rotation of the jaw members, so that, when the push-pull rod is slid forward, in particular to close the tool, the result is a gear ratio that allows a great transmission of force. These medical instruments have proved themselves in practice; however, in tight spaces—for instance, in endoscopic surgery—that have the disadvantage that the jointed gear in opening the jaw members rotate outward and thus greatly increase the diameter of the instrument in the area between the push-pull rod and the tool. This required space, however, is not always available and thus these known instruments cannot be employed in all operations.

Consequently it is the object of the invention to design a medical instrument of the aforementioned type in such a way that the instrument can be used even in closely confined spaces and with sufficient transmission of force.

SUMMARY OF THE INVENTION

This object is fulfilled according to the invention in a manner characterized in that the point of rotation is configured as a variable, virtual point of rotation that depends on the position of the jaw members with respect to one another.

Because of the inventive configuration of the point of rotation as a variable, virtual point of rotation dependent on the jaw position, the radial motion of the gear mechanism pointing from the instrument longitudinal axis to the outside in the area of the point of rotation is so reduced that the gear mechanism for moving the jaw members independently of the position of the jaw members to one another always lies within the instrument diameter.

According to a first practical embodiment of the invention, it is proposed that both jaw members should be rotatably configured and mounted on two axes that are mounted in the shaft crosswise to the instrument's longitudinal axis. Because of the mounting of the jaw members on two axes positioned in the shaft, the radial motion of the jaw members can be clearly reduced in the area of the point of rotation.

Coupling of the rotatable jaw members with the axes mounted in the shaft takes place, according to the invention, advantageously by means of two coupling gears each per jaw member, so that the coupling gears ensured an increased power transmission ratio between the push-pull rod and the jaw members, in comparison with instruments known in the art.

It is proposed, with a preferred embodiment of the invention, that every coupling gear of each jaw member is positioned with one end on one of the axes and with the other end is positioned rotatably on a stud positioned immovably in the respective jaw member. As a result of the bilateral rotatable mounting of the coupling gears, the coupling gears of each jaw member move in dependency on the respective working position of the jaw members relative to one another, so that in each case a best possible power transmission is ensured from the push-pull rod to the jaw members.

It is further proposed with the invention that the sectional point of the central axes of the jointed gear of one jaw member forms the point of rotation of the jaw members. This virtual point of rotation that moves according to the position of the jaw members with respect to one another has the effect that the gear mechanism for powering the jaw members independently of the position of the jaw members to one another, always lies within the instrument diameter, so that a medical instrument of this configuration can be used even in confined spaces such as are common, for instance, in endoscopic surgery.

According to a preferred embodiment of the invention, it is proposed that open spaces for the axes should be configured in the jaw members so that the axes, on which the coupling gear is mounted, penetrate the jaw members without any effect on the jaw members, and the jaw members that are positioned on the axes by means of the jointed gears can be moved with exactitude into the respective working position while rotating by means of the push-pull rod.

With a second practical embodiment of the invention it is proposed that both jaw members should be configured so that they can rotate by two coupling gears each, so that every coupling gear of each jaw member is positioned so that it can rotate with one end immovably positioned on a stud positioned on the respective jaw member and with the other end rotatably mounted on an axle neck that is positioned immovably on the side of the shaft closer to this jaw member.

In this embodiment the sectional point of the central axis of the coupling gear of one jaw member forms the point of rotation of the jaw members that is variable and dependent on the particular jaw member position.

According to another inventive embodiment, it is proposed that both jaw members are configured so that they can rotate by means of one coupling gear each, and here each coupling gear of each jaw member is mounted rotatably with one end immovable on a stud positioned on the respective jaw member and is mounted on an axle with the other end rotatably mounted on an axle neck positioned immovably on the side of the shaft close to this jaw member.

Finally, it is proposed with the invention that the push-pull rod of the medical instrument that can be used preferably for endoscopic purposes should be connected on the distal side by means of one steering gear each with each rotatable jaw member. The use of the steering gear constitutes a structurally simple configuration, in order to be able to rotate two jaw members on the jaw members starting from a push-pull rod with good power transmission onto the jaw members.

In addition, it is proposed with the invention that in every jaw member there should be a guide track for inserting a mounting pin positioned on the closer side of the shaft, in order to facilitate the guiding rotation of the jaw members.

The variable rotation point of the jaw members is formed in this embodiment by means of the intersection point of the central axle of the coupling gear of a jaw member with the guide track.

To form the instrument shaft, it is further proposed with the invention that the distal end of the shaft should be fork-shaped and include two studs running essentially parallel to one another and the proximal ends of the jaw members should be mounted between the studs. This structural design of the instrument shaft facilitates the insertion and removal of the instrument for cleaning purposes. The axles, on which the jaw members are positioned for guiding, are mounted in the shaft in the area of the studs.

Additional characteristics and advantages of the invention can be seen from the associated illustrations, in which three embodiments of an inventive medical instrument are presented in merely exemplary fashion, without restricting the invention to these embodiments.

BRIEF DESCRIPTION OF THE DRAWINGS

FIG. 7c shows a section along the line VIIc-VIIc according to FIG. 7a.

FIG. 8a shows a view according to FIG. 4 but depicting a third inventive embodiment.

FIG. 8b shows a view according to FIG. 8a but depicting the jaw members in opened condition.

DETAILED DESCRIPTION OF THE INVENTION

Figure 1:
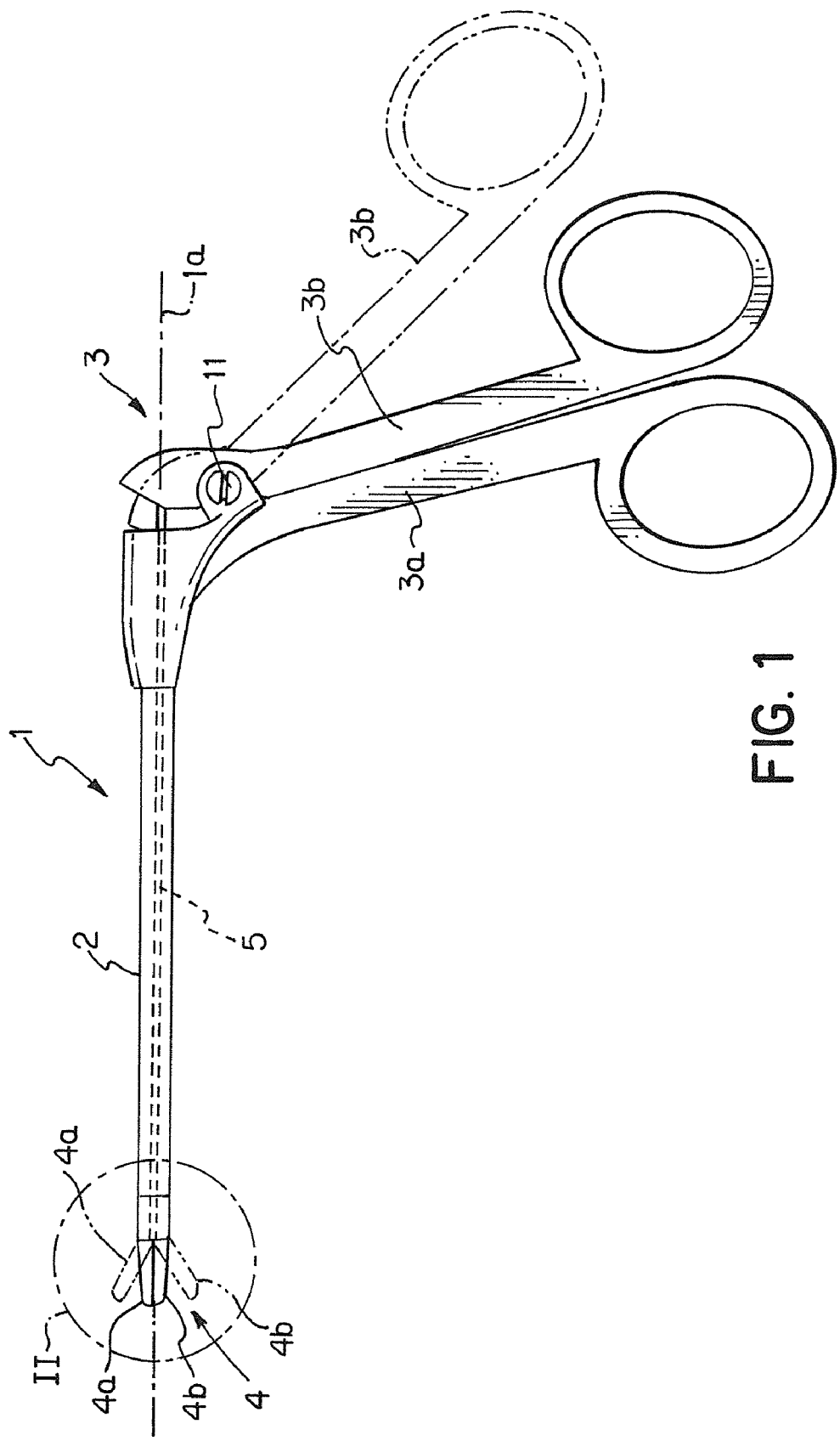
FIG. 1 shows a side view of an inventive medical instrument.

FIG. 1 shows the side view of a medical instrument whose force transmission mechanism has multiple uses, such as for punches, scissors, needle holders, gripping instruments, and the like.

The medical instrument 1 illustrated in exemplary form consists essentially of a hollow shaft 2 on whose proximal end a handle 3 is configured, which consists of a rigid gripping member 3a and a gripping member 3b that can rotate with respect to the rigid gripping member 3a. The distal end of the shaft 2 has a tool 4, which is made up of two rotatable jaw members 4a and 4b.

As can be seen in particular from the detail views of FIGS. 3, 4, and 6a to 6b, the jaw members 4a, 4b of the tool 4 and the rotatable gripping member 3b of the handle 3 are coupled with one another by means of a push-pull rod 5 mounted in the hollow shaft 2 in such a way that through the displacement of the gripping member 3b of the handle 3, the jaw members 4a and 4b of the tool 4 can be moved from the closed position (shown in darkened sections in FIG. And FIGS. 4, 6a, 7a, 8a, 9a, and 10a) into the open position (striped section in FIG. 1 and FIGS. 6b, 6c, 7b, and 8b) or vice versa. The respective related position of the rotatable gripping member 3b is also depicted in FIG. 1 as darkened (for the closed position) and striped (for an open position).

It can also be seen from FIGS. 4 and 6a through 7c that in these three embodiments the push-pull rod 5 is not directly connected with the jaw members 4a and 4b but rather through the intermediary of two toggle joints 6. The toggle joints 6 allow a good transmission of force from the push-pull rod 5 to the two jaw members 4a and 4b.

To ensure that in the first embodiment shown in FIGS. 2 through 6c, on the one hand a sufficient transmission of force can be applied for the required cutting or clamping forces of the push-pull rod 5 on the jaw members 4a and 4b and, on the other hand, the dimensions of the instrument are not enlarged by the gear mechanism, the jaw members 4a and 4b are positioned so that they control two axles 7 and 8, which in turn are mounted parallel to one another and perpendicular to the instrument longitudinal axis 1a in the shaft 2, so that in the jaw members 4a and 4b arc-shaped spaces are opened up for the axles 7 and 8.

The rotatable jaw members 4a and 4b are coupled with the axles 7 and 8 positioned in the shaft 2 by means of two pivot gears 10 and 11 per jaw member 4a, 4b, so that the pivot gears 10, 11 ensure an increased force transmission ratio between the push-pull rod 5 and the jaw members 4a, 4b.

Figure 4:
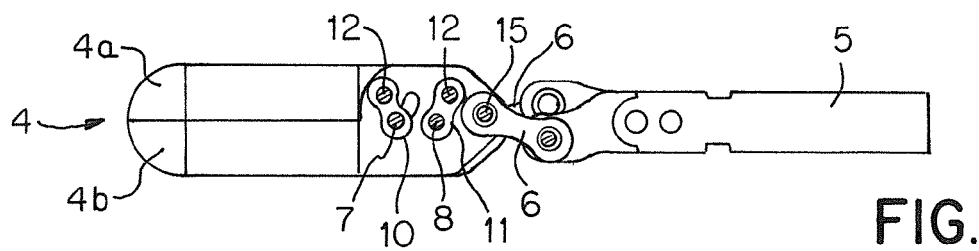
FIG. 4 shows a view according to FIG. 2, showing the medical instrument but without its shaft.
Figure 5:
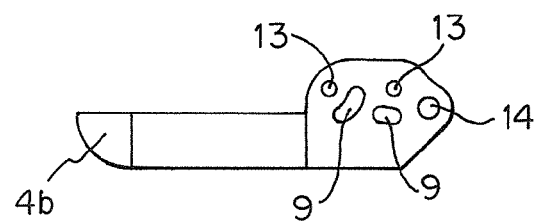
FIG. 5 shows a side view of the lower jaw member according to FIG. 4.

The structure of the jaw members 4a, 4b and their coupling with the pivot gears 10 and 11 is shown in particular from the comparison of FIGS. 4 and 5. Each pivot gear 10, 11 of every jaw member 4a, 4b is mounted with one end on one of the axles 7, 8 and with the other end rotatably mounted on a stud 12 positioned immovably in the respective jaw member 4a, 4b. From the jaw member 4b illustrated in sole position in FIG. 5, it is possible to see the various bearing points for the pivot gears 10 and 11 as well as the toggle joints 6, namely bearing bore-holes 13 for insertion of the studs 12, the arc-shaped openings 9 for the axles 7 and 8, and a bore-hole 14 for inserting a bearing stud 15 on the distal end of the toggle joint 6.

Figure 6A:
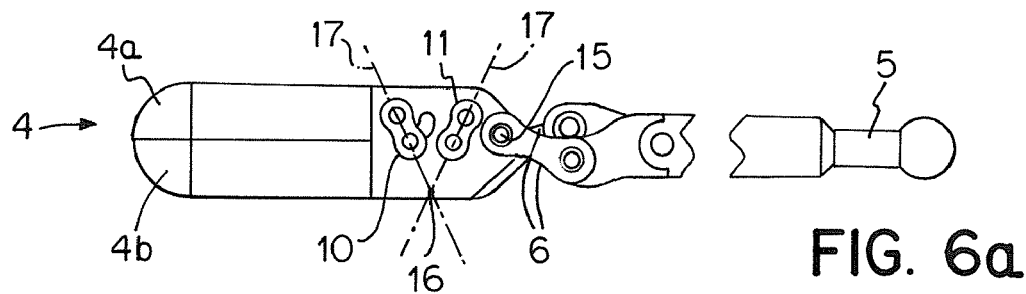
FIG. 6a shows a view according to FIG. 4, depicting the jaw members in closed position.
Figure 6B:
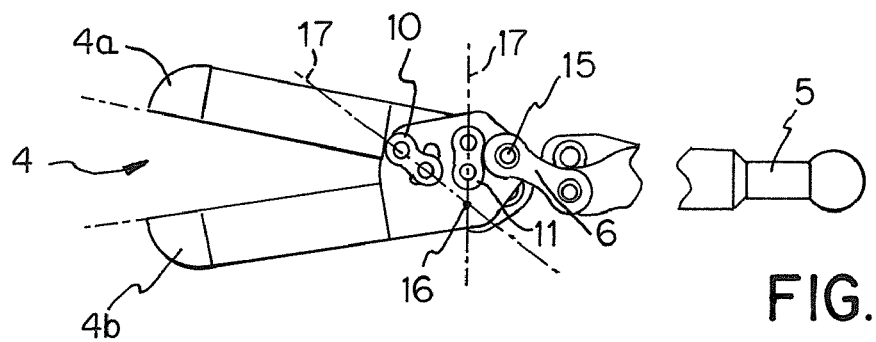
FIG. 6b shows a view according to FIG. 6a but depicting the jaw members in partly opened condition.
Figure 6C:
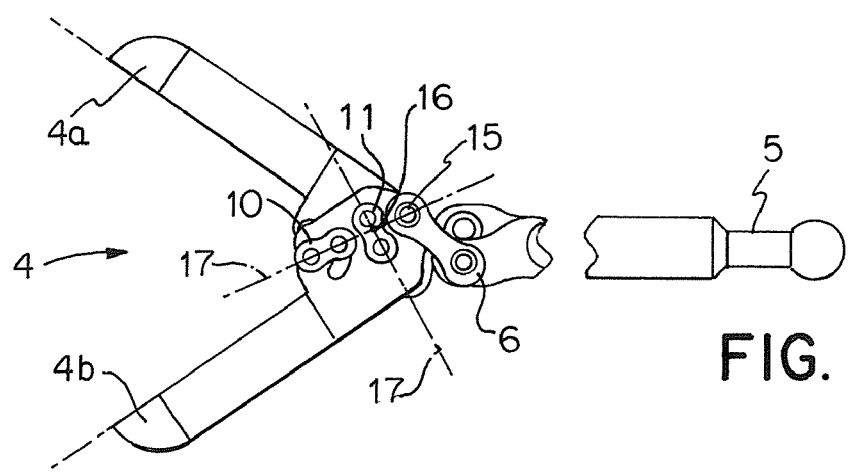
FIG. 6c shows a view according to FIG. 6a but depicting the jaw members in completely opened position.

The manner of operation of a medical instrument 1 of this configuration is depicted in FIGS. 6a through 6c, which show the jaw members 4a and 4b in three different working positions.

Because of the positioning of the jaw members 4a and 4b by means of the pivot gears 10 and 11 on the two parallel axles 7 and 8, there is no immovable point of rotation around which the two jaw members 4a and 4b can turn from the closed position shown in FIG. 6a all the way to the completely opened position shown in FIG. 6c. The rotation point of the jaw members 4a and 4b, in the illustrated first structural embodiment, results from the intersection 16 of the two center axes 17 of the pivot gears 10 and 11 of each jaw member 4a, 4b.

As can be seen from FIGS. 6a to 6c, from this construction there results a variable rotation point for the jaw members 4a, 4b so that, independently of the position of the jaw members 4a, 4b to one another, the toggle mechanism for powering the jaw members 4a and 4b always lies within the instrument diameter, so that a medical instrument 1 of this configuration can be used even in narrow spaces such as in endoscopic surgery.

Figure 2:
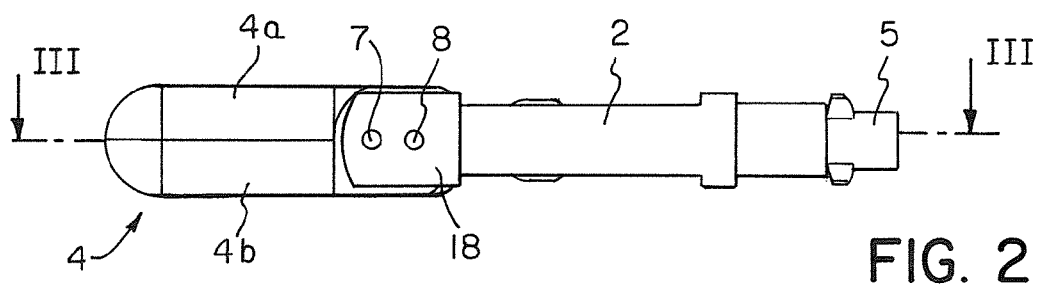
FIG. 2 shows an enlarged view of detail II from FIG. 1, depicting a first embodiment.
Figure 3:
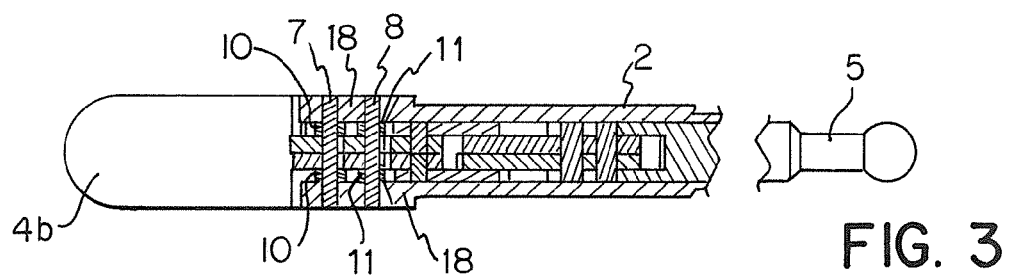
FIG. 3 shows a section along the line III-III according to FIG. 1.

The distal end of the shaft 2, in the embodiment illustrated in FIGS. 2 and 3, is configured as fork-shaped consisting of two studs 18 running essentially parallel to one another, so that the proximal ends of the jaw members 4a, 4b are positioned between the studs 18 on the axles 7 and 8. This structural configuration of the instrument shaft 2 facilitates the installation and removal of the instrument 1 for cleaning purposes.

Figure 7A:
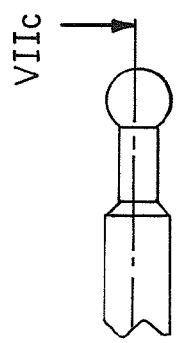
FIG. 7a shows a view according to FIG. 4 but depicting a second inventive embodiment.
Figure 7A:
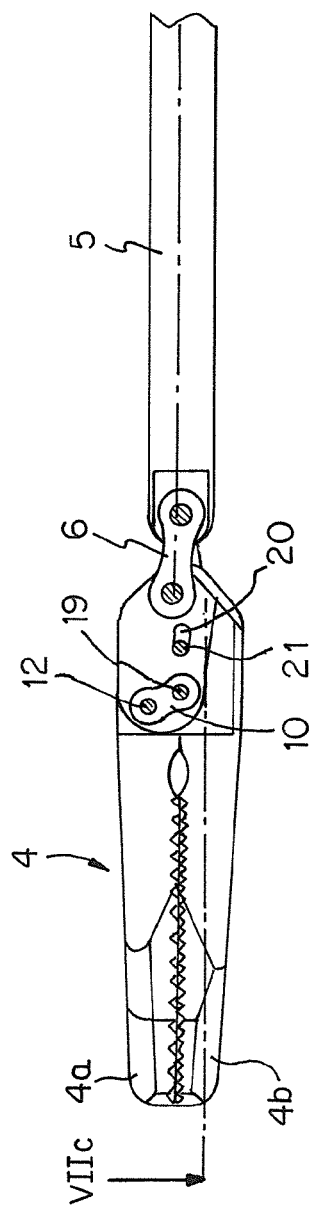
Figure 7B:
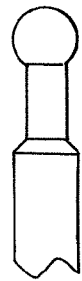
FIG. 7b shows a view according to FIG. 7a but depicting the jaw members in opened position.
Figure 7B:
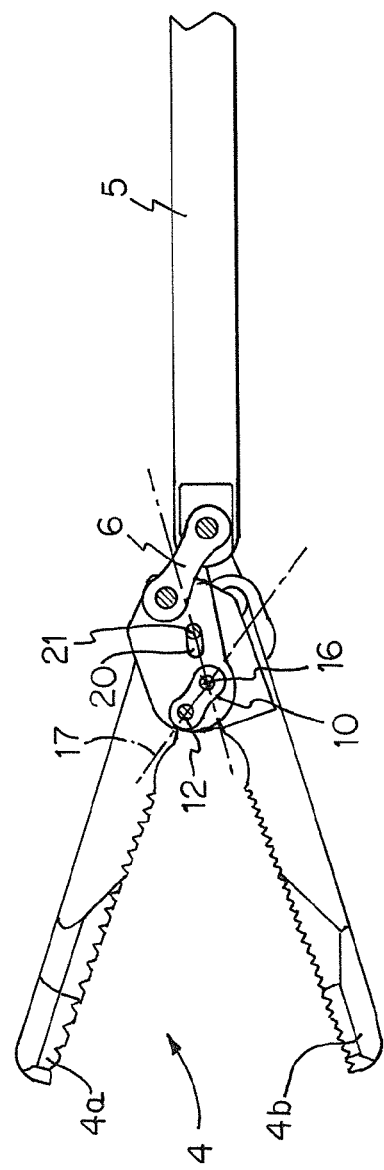

The second embodiment of the power transmission mechanism, shown in FIGS. 7a to 7c, between the push-pull rod 5 and the jaw members 4a and 4b is differentiated from the previously described embodiment in that in this embodiment each of the two jaw members 4a and 4b.

The second embodiment of the force transmission mechanism, shown in FIGS. 7a through 7c, between the push-pull rod 5 and the jaw members 4a and 4b, is distinguished from the previously described embodiment in that in this version each of the two jaw members 4a and 4b is coupled with the shaft 2 by only one pivot gear 10.

In this embodiment this coupling is performed in such a way that every pivot gear 10 of each jaw member 4a, 4b is rotatably mounted with one end immovably positioned on a stud 12 situated on the respective jaw member 4a, 4b and with the other end rotatably mounted on an axle neck 19 positioned immovably on the side of the shaft closer to this jaw member 4a, 4b.

As an alternative to the one-sided mounting of the pivot gear on the axle neck 19, it is also possible to position the pivot gear 10 on continuous axles, although in this embodiment openings should be provided for the axles in the jaw members 4a and 4b.

In addition, in each jaw member 4a, 4b a guide track 20 is configured for inserting a bearing pin 21 that is positioned on the closer side of the shaft and serves to support the rotation of the jaw members 4a and 4b. The rotation point 16 of the jaw members 4a, 4b is configured in this embodiment by the intersection 16 of the central axle 17 of the pivot gear 10 of one jaw member 4a, 4b with the guide track 20.

FIGS. 8a and 8b show a third embodiment of the force transmission mechanism between the push-pull rod 5 and the jaw members 4a and 4b. This embodiment, in contrast to the two previously described structural embodiments, has the essential difference that the push-pull rod 5 is not connected with the jaw members 4a and 4b by an intermediate toggle joint 6 but rather directly by means of a bearing bolt 22.

In addition, the third embodiment, shown in FIGS. 8a and 8b, is distinguished from the two versions previously described and shown in FIGS. 7a through 7c in that here no guide tracks for bearing pins are provided in the jaw members 4a and 4b. Instead, the rotatable jaw members 4a, 4b are coupled with the shaft 2 entirely by one pivot gear 10 each, which is mounted with one end rotatably but immovably on a stud 12 mounted on the respective jaw member 4a, 4b and with the other end rotatably mounted on an axle neck 9 positioned immovably on the side of the shaft closer to this jaw member 4a, 4b.

In both embodiments the jaw members 4a and 4b are coupled with the shaft 2 by one axle neck 23 each, which forms a bearing connection of the respective jaw member 4a, 4b with the closer side of the shaft 2.

As an alternative to unilateral mounting of the pivot gear 10 on the axle neck 19, it is also possible to position the pivot gear 10 on continuous axles, although in this embodiment openings should be provided for the axles in jaw members 4a and 4b.

In the position illustrated in FIG. 8a with closed jaw members 4a, 4b, the pivot gear 10 connects the shaft 2, with which it is linked by the lower rotation point (stud 19), with the respective jaw member 4a, 4b, with the pivot gear 10 by which the upper rotation point (stud 12) is connected.

In the position shown in FIG. 8b with open jaw members 4a, 4b, the pivot gear 10 connects the shaft 2, with which it is connected with the proximal rotation point (stud 19), with the respective jaw member 4a, 4b, with the pivot gear 10 consequently by the distal rotation point (stud 12) is connected. Thus in this embodiment the rotation point moves approximately in a quarter-circular motion.

What is claimed is:

1. A medical instrument with a shaft whose proximal end is provided with a handle consisting of two gripping members and whose distal end is provided with a tool consisting of two jaw members and in which, to open and close the tool, at least one jaw member can rotate with respect to the other jaw member around a point of rotation by means of a push-pull rod and in which the push-pull rod is connected on the proximal side with a rotatable gripping member of the handle, characterized in that both jaw members are configured so that they can rotate and are mounted on two axles that are mounted in the shaft perpendicularly to the longitudinal axis of the instrument, wherein arc-shaped openings are cleared for said two axles in the jaw members, and in that the rotation point is configured as a virtual rotation point that varies depending on the position of the jaw members with respect to one another, further characterized in that each jaw member is coupled with the axles by two pivot gears each and each pivot gear of every jaw member being positioned with one end on one of the axles and with the other end rotatably situated on a stud positioned immovably in the respective jaw member wherein said pivot gears are not directly connected to said push-pull rod.

2. A medical instrument according to claim 1, characterized in that the intersection of the central axes of the pivot gears of one jaw member forms the rotation point of the jaw members.

3. A medical instrument according to claim 1, characterized in that the distal end of the shaft is in fork shape consisting of two studs running essentially parallel to one another and the proximal ends of the jaw members are positioned between the studs.

4. A medical instrument according to claim 3, characterized in that the axles are positioned in the shaft in the area of the studs.

5. A medical instrument according to any one of claim 1, characterized in that the push-pull rod is connected on the distal side with each rotatable jaw member by one toggle joint each.

6. A medical instrument according to claim 1, characterized in that the medical instrument is an endoscopic instrument.

7. A medical instrument with a shaft whose proximal end is provided with a handle consisting of two gripping members and whose distal end is provided with a tool consisting of two jaw members and in which, to open and close the tool, at least one jaw member can rotate with respect to the other jaw member around a point of rotation by means of a push-pull rod and in which the push-pull rod is connected on the proximal side with a rotatable gripping member of the handle, characterized in that both jaw members are configured so that they can rotate and are mounted on two axles that are mounted in the shaft perpendicularly to the longitudinal axis of the instrument, wherein arc-shaped openings are cleared for said two axles in the jaw members, and in that the rotation point is configured as a virtual rotation point that varies depending on the position of the jaw members with respect to one another, characterized in that both jaw members are configured so that they can rotate each around two pivot gears, while each pivot gear of every jaw member is positioned rotatably with one end immovable on a stud positioned on the respective jaw member and with the other end rotatably positioned on an axle neck situated immovably on the side of the shaft closer to this jaw member; wherein said pivot gears are not directly connected to the push-pull rod.

8. A medical instrument according to claim 7, characterized in that the intersection of the central axes of the pivot gears of one jaw member forms the rotation point of the jaw members.

* * * * *